United States Patent [19]

Audousset et al.

[11] Patent Number: 5,769,903
[45] Date of Patent: *Jun. 23, 1998

[54] COMPOSITION FOR THE OXIDATION DYEING OF KERATIN FIBERS, COMPRISING AN OXIDATION BASE, AN INDOLE COUPLER AND AN ADDITIONAL HETEROCYCLIC COUPLER, AND DYEING PROCESS

[75] Inventors: Marie-Pascale Audousset, Asnieres; Jean Cotteret, Verneuil sur Seine, both of France

[73] Assignee: L'Oreal, Paris, France

[*] Notice: The term of this patent shall not extend beyond the expiration date of Pat. No. 5,683,474.

[21] Appl. No.: 838,062

[22] Filed: Apr. 17, 1997

Related U.S. Application Data

[63] Continuation of Ser. No. 607,720, Feb. 27, 1996, abandoned.

[30] Foreign Application Priority Data

Feb. 27, 1995 [FR] France ................................. 95 02270

[51] Int. Cl.⁶ ................................................... A61K 7/13
[52] U.S. Cl. ........................... 8/409; 8/406; 8/408; 8/410; 8/423; 8/565; 8/568; 8/569; 8/573; 8/574; 8/576
[58] Field of Search ........................... 8/406, 408, 409, 8/410, 423, 565, 568, 569, 573, 574, 576

[56] References Cited

U.S. PATENT DOCUMENTS

| | | | |
|---|---|---|---|
| 5,034,015 | 7/1991 | Junino et al. | 8/423 |
| 5,061,289 | 10/1991 | Clausen et al. | 8/405 |
| 5,131,911 | 7/1992 | Lang et al. | 8/405 |
| 5,135,544 | 8/1992 | Grollier et al. | 8/408 |
| 5,207,798 | 5/1993 | Cotteret et al. | 8/408 |
| 5,354,870 | 10/1994 | Lang et al. | 548/469 |
| 5,380,340 | 1/1995 | Neunhoeffer et al. | 8/409 |
| 5,391,206 | 2/1995 | Cotteret | 8/408 |
| 5,518,505 | 5/1996 | Cotteret | 8/408 |
| 5,542,952 | 8/1996 | Genet et al. | 8/408 |

FOREIGN PATENT DOCUMENTS

| | | |
|---|---|---|
| A-0375977 | 7/1990 | European Pat. Off. . |
| A-0428441 | 5/1991 | European Pat. Off. . |
| A-0446132 | 9/1991 | European Pat. Off. . |
| A-0459901 | 12/1991 | European Pat. Off. . |
| A-0465339 | 1/1992 | European Pat. Off. . |
| A-0465340 | 1/1992 | European Pat. Off. . |
| A-0634164 | 1/1995 | European Pat. Off. . |
| A-2362112 | 3/1978 | France . |
| A-1916139 | 11/1969 | Germany . |
| A-2359399 | 6/1975 | Germany . |
| A-3031709 | 4/1982 | Germany . |
| A-3743769 | 7/1989 | Germany . |
| A-3930446 | 3/1990 | Germany . |
| A-3843892 | 6/1990 | Germany . |
| 3942294 | 6/1991 | Germany . |
| A-4133957 | 4/1993 | Germany . |
| A-1026978 | 4/1966 | United Kingdom . |
| A-1153196 | 5/1969 | United Kingdom . |
| A-1217479 | 12/1970 | United Kingdom . |
| A-2180215 | 3/1987 | United Kingdom . |
| WO-A-9309759 | 5/1993 | WIPO . |
| WO-A-9408969 | 4/1994 | WIPO . |
| WO-A-9408970 | 4/1994 | WIPO . |

OTHER PUBLICATIONS

English language translation of DE 3,031,709, Wella AG, pp. 1–12, Apr. 1982.
English Derwent Abstract of EP–A–0428441, May 1991.
English Derwent Abstract of EP–A–0465339, Jan. 1992.
English Derwent Abstract of EP–A—459901, Dec. 1991.
English Derwent Abstract of JP 2019576, Jan. 1990.
English Derwent Abstract of JP 5163124, Jun. 1993.
English Derwent Abstract of WO–A–9408969, Apr. 1994.
English Derwent Abstract of WO–A–9408970, Apr. 1994.
English Derwent Abstract of DE–A–2359399, Jun. 1975.
English Derwent Abstract of DE–A–3843892, Jun. 1990.
English Derwent Abstract of DE–A–3743769, Jul. 1989.
English Derwent Abstract of DE–A–3031709, Apr. 1978.
English Derwent Abstract of FR–A–2362112, Apr. 1978.

*Primary Examiner*—Paul Lieberman
*Assistant Examiner*—Caroline L. Dusheck
*Attorney, Agent, or Firm*—Finnegan, Henderson, Farabow, Garrett & Dunner, L.L.P.

[57] ABSTRACT

The present invention relates to a composition for the oxidation dyeing of keratin fibers, in particular human keratin fibers such as the hair, comprising an oxidation base in combination with at least one suitably selected indole coupler and at least one additional heterocyclic coupler which is also suitably selected, as well as to the dyeing process using this composition with an oxidizing agent.

36 Claims, No Drawings

COMPOSITION FOR THE OXIDATION DYEING OF KERATIN FIBERS, COMPRISING AN OXIDATION BASE, AN INDOLE COUPLER AND AN ADDITIONAL HETEROCYCLIC COUPLER, AND DYEING PROCESS

This application is a continuation of application Ser. No. 08/607,720, filed Feb. 27, 1996, now abandoned.

The present invention relates to a composition for the oxidation dyeing of keratin fibers, in particular human keratin fibers such as the hair, comprising an oxidation base in combination with, on the one hand, at least one suitably selected indole coupler and, on the other hand, at least one additional heterocyclic coupler which is also suitably selected, as well as to the dyeing process using this composition with an oxidizing agent.

It is known to dye keratin fibers, and in particular human hair, with dye compositions containing oxidation dye precursors, in particular ortho- or para-phenylenediamines, ortho- or para-aminophenols, and heterocyclic compounds such as diaminopyrazole derivatives, which are generally referred to as oxidation bases. The oxidation dye precursors, or oxidation bases, are colorless or weakly colored compounds which, when combined with oxidizing products, may give rise to colored compounds and dyes by a process of oxidative condensation.

It is also known that the shades obtained with these oxidation bases may be varied by combining them with couplers or coloration modifiers, the latter being chosen in particular from aromatic meta-diamines, meta-aminophenols, meta-diphenols and certain heterocyclic compounds such as indole derivatives and in particular 4-hydroxyindole.

The variety of molecules used as oxidation bases and couplers makes it possible to obtain a wide range of colors.

The so-called "permanent" coloration obtained by means of these oxidation dyes should highly preferably, moreover, satisfy a certain number of requirements. Thus, it should highly preferably have no toxicological drawbacks and it should highly preferably allow shades of the desired intensity to be obtained and have good resistance to external agents (light, inclement weather, washing, permanent waving, perspiration and friction).

The dyes should highly preferably also allow white hairs to be covered and they should highly preferably be as unselective as possible, i.e., they should highly preferably allow the smallest possible differences in coloration, i.e., low selectivity, to be produced over the entire length of the same keratin fiber, which may indeed be differently sensitized (i.e. damaged) between its tip and its root.

Compositions for the oxidation dyeing of keratin fibers, containing an oxidation base in combination with a heterocyclic coupler such as, for example, 4-hydroxy-1,2-methylenedioxybenzene, 4-amino-1,2-methylenedioxybenzene, 4-hydroxyindole or 6-hydroxybenzomorpholine, have already been proposed, in particular in German patent applications DE 3,031,709 and DE 3,743,769, French patent application FR 2,362,112 and European patent application EP 459,901. Such compositions make it possible to achieve varied ranges of shades; however, they are not entirely satisfactory, in particular from the point of view of the resistance of the colorations obtained to the various attacking factors to which the hair may be subjected.

The inventors have discovered that it is possible to obtain novel unselective and particularly resistant dyes, which are capable of giving rise to strong colorations in varied shades, by combining at least one oxidation base, at least one suitably selected indole coupler and at least one additional heterocyclic coupler which is also suitably selected and is different from the said indole coupler. This discovery forms the basis of the present invention.

The subject of the invention is thus a composition for the oxidation dyeing of keratin fibers, and in particular human keratin fibers such as the hair, characterized in that it comprises, in a medium which is suitable for dyeing:

(a) at least one oxidation base, (b) at least one coupler selected from indole couplers of the following formula (I) and the acid addition salts thereof:

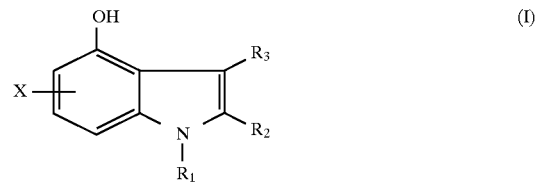

in which:

$R_1$ represents a hydrogen atom or a $C_1$–$C_4$ alkyl radical, $R_2$ and $R_3$, which may be identical or different, represent a hydrogen atom or a $C_1$–$C_4$ alkyl, carboxyl or ($C_1$–$C_4$)alkoxycarbonyl radical, X represents a hydrogen or halogen atom or a $C_1$–$C_4$ alkyl, $C_1$–$C_{18}$ alkoxy or acetylamino radical;

(c) at least one additional heterocyclic coupler chosen from:

(i) the indole derivatives of following formula (III), and the acid-addition salts thereof:

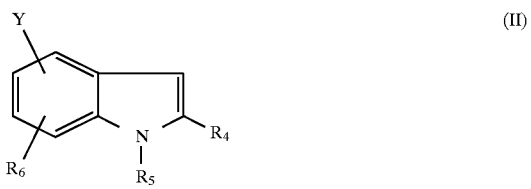

in which:

$R_4$ and $R_5$, which may be identical or different, represent a hydrogen atom or a $C_1$–$C_4$ alkyl radical;

$R_6$ represents a hydrogen atom or a $C_1$–$C_4$ alkyl or hydroxyl radical;

Y represents a hydroxyl radical or a radical $NHR_7$ in which $R_7$ represents a hydrogen atom or a $C_1$–$C_4$ alkyl or $C_1$–$C_4$ hydroxyalkyl radical;

with the proviso that:
when $R_6$ denotes hydroxyl, it then occupies the 6-position, Y denotes hydroxyl and occupies the 5-position and $R_4$ and $R_5$ represent a hydrogen atom,
when Y denotes hydroxyl, it then occupies the 6- or 7-position, and $R_6$ is other than hydroxyl,
when Y denotes amino, it then occupies the 4-, 6- or 7-position;

(ii) the benzimidazole derivatives of following formula (III), and the acid-addition salts thereof:

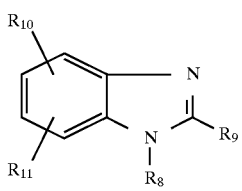

(III)

in which:
$R_8$ represents a hydrogen atom or a $C_1$–$C_4$ alkyl radical,
$R_9$ represents a hydrogen atom or a $C_1$–$C_4$ alkyl or phenyl radical,
$R_{10}$ represents a hydroxyl, amino or methoxy radical,
$R_{11}$ represents a hydrogen atom or a hydroxyl, methoxy or $C_1$–$C_4$ alkyl radical;
with the proviso that:
when $R_{10}$ denotes an amino radical, it then occupies the 4-position,
when $R_{10}$ occupies the 4-position, $R_{11}$ then occupies the 7-position,
when $R_{10}$ occupies the 5-position, $R_{11}$ then occupies the 6-position;
(iii) the benzomorpholine derivatives of following formula (IV), and the acid-addition salts thereof:

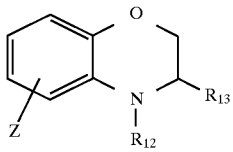

(IV)

in which:
$R_{12}$ and $R_{13}$, which may be identical or different, represent a hydrogen atom or a $C_1$–$C_4$ alkyl radical,
Z represents a hydroxyl or amino radical;
(iv) the pyridine derivatives of following formula (V), and the acid-addition salts thereof:

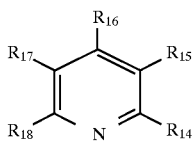

(V)

in which:
$R_{14}$ represents a hydrogen atom, a hydroxyl, $C_1$–$C_4$ alkoxy, $C_1$–$C_4$ monohydroxyalkoxy, $C_2$–$C_4$ polyhydroxyalkoxy or amino radical or the —OCH$_2$CH$_2$COCH$_2$CH$_2$OH group,
$R_{15}$ and $R_{17}$, which may be identical or different, represent a hydrogen atom or a hydroxyl, amino or $C_1$–$C_4$ alkyl radical,
$R_{16}$ represents a hydrogen atom or a $C_1$–$C_4$ alkyl radical,
$R_{18}$ represents a hydrogen atom or a hydroxyl, $C_1$–$C_4$ alkoxy, $C_1$–$C_4$ monohydroxyalkoxy, $C_2$–$C_4$ polyhydroxyalkoxy or amino radical,
with the proviso that when $R_{14}$ represents a polyhydroxyalkoxy radical or the —OCH$_2$CH$_2$COCH$_2$CH$_2$OH group, $R_{15}$ and $R_{17}$ then represent an amino radical;
and it being understood that these compounds of formula (V) contain not more than two substituted or unsubstituted amino groups or not more than two hydroxyl groups or not more than one amino group and one hydroxyl group per molecule, these amino and/or hydroxyl groups necessarily being in a meta position relative to each other;

(v) the indoline derivatives chosen from 6-hydroxyindoline, 6-aminoindoline and 5,6-dihydroxyindoline, and the acid-addition salts thereof;
(vi) the quinoline derivatives of following formula (VI), and the acid-addition salts thereof:

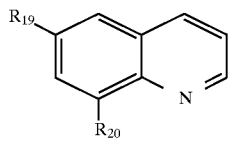

(VI)

in which:
$R_{19}$ denotes a hydroxyl or $C_1$–$C_4$ alkoxy radical,
$R_{20}$ denotes a hydrogen atom or an amino radical;
(vii) the sesamol derivatives of following formula (VII), and the acid-addition salts thereof:

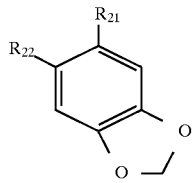

(VII)

in which:
$R_{21}$ denotes a hydroxyl or amino radical,
$R_{22}$ denotes a halogen atom or a $C_1$–$C_4$ alkoxy radical.

The oxidation dye composition in accordance with the invention makes it possible to obtain colorations in varied shades, which are unselective and have excellent properties of resistance both to atmospheric agents such as light and inclement weather and to perspiration and the various treatments to which the hair may be subjected (shampooing, permanent waving).

The subject of the invention is also a process for the oxidation dyeing of keratin fibers using this composition.

The oxidation base or bases which may be used in the context of the dye compositions in accordance with the invention are preferably chosen from para-phenylenediamines, bis(phenyl)alkylenediamines, para-aminophenols, ortho-aminophenols and heterocyclic bases, and the acid-addition salts thereof.

The acid-addition salts which may be used in the context of the dye compositions of the invention are chosen in particular from the hydrochlorides, hydrobromides, sulphates and tartrates.

Among the para-phenylenediamines which may be used as oxidation bases in the context of the compositions in accordance with the invention, mention may be made in particular of the compounds corresponding to the following formula (VIII), and the acid-addition salts thereof:

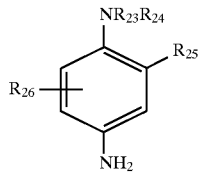

(VIII)

in which:
$R_{23}$ represents a hydrogen atom or a $C_1$–$C_4$ alkyl, $C_1$–$C_4$ monohydroxyalkyl, $C_2$–$C_4$ polyhydroxyalkyl or ($C_1$–$C_4$)alkoxy($C_1$–$C_4$)alkyl radical,
$R_{24}$ represents a hydrogen atom or a $C_1$–$C_4$ alkyl, $C_1$–$C_4$ monohydroxyalkyl or $C_2$–$C_4$ polyhydroxyalkyl radical, $R_{25}$ represents a hydrogen atom, a halogen atom such as a chlorine atom, or a $C_1$–$C_4$ alkyl, sulpho, carboxyl, $C_1$–$C_4$ monohydroxyalkyl or $C_1$–$C_4$ hydroxyalkoxy radical, $R_{26}$ represents a hydrogen atom or a $C_1$–$C_4$ alkyl radical.

In the above para-phenylenediamine formula (VIII), and when $R_{26}$ is other than a hydrogen atom, $R_{23}$ and $R_{24}$ then preferably represent a hydrogen atom and $R_{25}$ is preferably identical to $R_{26}$, and when $R_{25}$ represents a halogen atom, $R_{23}$, $R_{24}$ and $R_{26}$ then preferably represent a hydrogen atom.

Among the para-phenylenediamines of above formula (VIII) which may be mentioned more particularly are para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-(β-methoxyethyl) aminobenzene, 2-chloro-para-phenylenediamine, and the acid-addition salts thereof.

Among the bis(phenyl)alkylenediamines which may be used as oxidation bases in the context of the compositions in accordance with the invention, mention may be made more particularly of the compounds corresponding to the following formula (IX), and the acid-addition salts thereof:

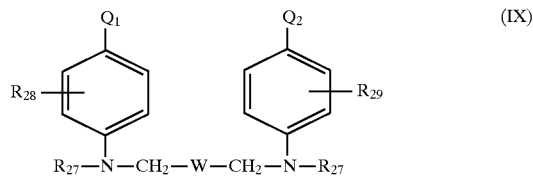

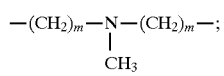

in which:

$Q_1$ and $Q_2$, which may be identical or different, represent a hydroxyl radical or a radical $NHR_{30}$ in which $R_{30}$ represents a hydrogen atom or a $C_1$–$C_4$ alkyl radical, $R_{27}$ independently represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue may be substituted, $R_{28}$ and $R_{29}$, which may be identical or different, represent a hydrogen or halogen atom or a $C_1$–$C_4$ alkyl radical, W represents a radical, the radical being —$(CH_2)_n$—; —$(CH_2)_m$—O—$(CH_2)_m$—; —$(CH_2)_m$—CHOH—$(CH_2)_m$— or in which n is an integer from 0 to 8 and m is independently an integer from 0 to 4.

Among the bis(phenyl)alkylenediamines of above formula (IX) which may be mentioned more particularly are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N N'-bis(4-methylaminophenyl)tetramethylenediamine, N,N'-bis(ethyl)-N,N'-bis(4'-amino-3'-methylphenyl)ethylenediamine, and the acid-addition salts thereof.

Among these bis(phenyl)alkylenediamines of formula (IX), N,N'-bis(β-hydroxyethyl)-N,N'-bis(4'-aminophenyl)-1,3-diaminopropanol or one of the acid-addition salts thereof is particularly preferred.

Among the para-aminophenols which may be used as oxidation bases in the context of the compositions in accordance with the invention, mention may be made more particularly of the compounds corresponding to the following formula (X), and the acid-addition salts thereof:

in which:

$R_{31}$ represents a hydrogen atom or a $C_1$–$C_4$ alkyl, $C_1$–$C_4$ monohydroxyalkyl, $(C_1$–$C_4)$alkoxy$(C_1$–$C_4)$alkyl or $C_1$–$C_4$ aminoalkyl radical, $R_{32}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $(C_1$–$C_4)$alkoxy$(C_1$–$C_4)$alkyl radical, it being understood that at least one of the radicals $R_{31}$ or $R_{32}$ represents a hydrogen atom.

Among the para-aminophenols of above formula (X) which may be mentioned more particularly are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and the acid-addition salts thereof.

Among the ortho-aminophenols which may be used as oxidation bases in the context of the compositions in accordance with the invention, mention may be made more particularly of 2-aminophenol, 2-amino-1-hydroxy-5-methylbenzene, 2-amino-1-hydroxy-6-methylbenzene, 5-acetamido-2-aminophenol, and the acid-addition salts thereof.

Among the heterocyclic bases which may be used as oxidation bases in the context of the compositions in accordance with the invention, mention may be made more particularly of pyridine derivatives, pyrimidine derivatives, pyrazole derivatives, and the acid-addition salts thereof.

Among the pyridine derivatives which may be mentioned more particularly are the compounds described, for example, in GB patents 1,026,978 and 1,153,196, such as 2,5-diaminopyridine, and the acid-addition salts thereof. The disclosures of said GB patents are hereby incorporated by reference.

Among the pyrimidine derivatives which may be mentioned more particularly are the compounds described, for example, in German patent DE 2,359,399 or Japanese patents JP 88-169,571 and JP 91-333,495, such as 2,4,5,6-tetraaminopyrimidine, 4-hydroxy-2,5,6-triaminopyrimidine, and the acid-addition salts thereof. The disclosures of said German and Japanese patents are hereby incorporated by reference.

Among the pyrazole derivatives which may be mentioned more particularly are the compounds described in patents DE 3,843,892 and DE 4,133,957 and patent applications WO 94/08969 and WO 94/08970, such as 4,5-diamino-1-methylpyrazole, 3,4-diaminopyrazole, and the acid-addition salts thereof. The disclosures of said German and PCT patents are hereby incorporated by reference.

Among the indole couplers of above formula (I) which may be mentioned more particularly are 4-hydroxyindole, 4-hydroxy-5-ethoxyindole, 4-hydroxy-5-methoxyindole, 4-hydroxy-1-methyl-5-ethoxyindole, 4-hydroxy-2-ethoxycarbonyl-5-ethoxyindole, 4-hydroxy-2-methyl-5-ethoxyindole, 4-hydroxy-5-methylindole, 4-hydroxy-2-methylindole, 4-hydroxy-1-methylindole, and the acid-addition salts thereof.

Among the indole derivatives of above formula (II) which may be used as additional heterocyclic couplers in the compositions in accordance with the invention, mention may be made more particularly of 6-hydroxyindole, 7-aminoindole, 6-aminoindole, 7-hydroxyindole, 7-ethyl-6-(β-hydroxyethyl)aminoindole, 4-aminoindole, 6-hydroxy-1-methylindole and 5,6-dihydroxyindole, and the acid-addition salts thereof.

Among the benzimidazole derivatives of above formula (III) which may be used as additional heterocyclic couplers in the compositions in accordance with the invention, mention may be made more particularly of 4-hydroxybenzimidazole, 4-amino-benzimidazole, 4-hydroxy-7-methylbenzimidazole, 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxy-benzimidazole, 5,6-dihydroxy-1-methylbenzimidazole, 5,6-dihydroxy-2-methylbenzimidazole and 5,6-dimethoxy-benzimidazole, and the acid-addition salts thereof.

Among the benzomorpholine derivatives of above formula (IV) which may be used as additional heterocyclic couplers in the compositions in accordance with the invention, mention may be made more particularly of 6-hydroxybenzomorpholine, N-methyl-6-hydroxybenzomorpholine and 6-aminobenzomorpholine, and the acid-addition salts thereof.

Among the pyridine derivatives of above formula (V) which may be used as additional heterocyclic couplers in the compositions in accordance with the invention, mention may be made more particularly of 2,6-dihydroxy-4-methylpyridine, 2,6-dihydroxy-3,4-dimethylpyridine, 3,5-diamino-2,6-dimethoxypyridine, 2,6-bis(β-hydroxyethyl)oxy-3,5-diaminopyridine, 3-amino-2,6-dimethoxy-5-hydroxypyridine, 2,6-diaminopyridine, 3-oxo-5-(3',5'-diamino-2'-pyridyloxy)pentanol and 3-(3',5'-diamino-2'-pyridyloxy)-2-hydroxypropanol, and the acid-addition salts thereof.

Among the quinoline derivatives of above formula (VI) which may be used as additional heterocyclic couplers in the compositions in accordance with the invention, mention may be made more particularly of 6-hydroxyquinoline and 8-amino-6-methoxyquinoline, and the acid-addition salts thereof.

Among the sesamol derivatives of above formula (VII) which may be used as additional heterocyclic couplers in the compositions in accordance with the invention, mention may be made more particularly of 2-bromo-4,5-methylenedioxyphenol and 1-amino-6-methoxy-3,4-methylenedioxybenzene, and the acid-addition salts thereof.

According to a particularly preferred embodiment of the invention, the oxidation dye compositions in accordance with the invention include at least one of the following ternary combinations:

(a): para-phenylenediamine,
(b): 4-hydroxyindole,
(c): 6-hydroxyindole;
(a): para-phenylenediamine,
(b): 4-hydroxyindole,
(c): 4-hydroxybenzimidazole;
(a): para-phenylenediamine,
(b): 4-hydroxyindole,
(c): 6-hydroxybenzomorpholine;
(a): para-aminophenol,
(b): 4-hydroxyindole,
(c): 6-hydroxyindole;
(a): 4-amino-3-methylphenol,
(b): 4-hydroxyindole,
(c): 6-hydroxyindole;
(a): 2-aminophenol,
(b): 4-hydroxyindole,
(c): 6-hydroxyindole;
(a): 4,5-diamino-1-methylpyrazole,
(b): 4-hydroxyindole,
(c): 6-hydroxyindole;
(a): 4,5-diamino-1-methylpyrazole,
(b): 4-hydroxyindole,
(c): 4-hydroxybenzimidazole;
(a): 4,5-diamino-1-methylpyrazole,
(b): 4-hydroxyindole,
(c): 6-hydroxybenzomorpholine;
(a): 2,6-dimethyl-para-phenylenediamine,
(b): 4-hydroxyindole,
(c): 6-hydroxyindole;
(a): 2,6-dimethyl-para-phenylenediamine,
(b): 4-hydroxyindole,
(c): 4-hydroxybenzimidazole;
(a): 2,6-dimethyl-para-phenylenediamine,
(b): 4-hydroxyindole,
(c): 6-hydroxybenzomorpholine,
(a): 2,6-hydroxyethyl-para-phenylenediamine,
(b): 4-hydroxyindole,
(c): 6-hydroxyindole;
(a): 2-β-hydroxyethyl-para-phenylenediamine,
(b): 4-hydroxyindole,
(c): 4-hydroxybenzimidazole;
(a): para-phenylenediamine,
(b): 4-hydroxy-1-N-methylindole,
(c): 6-hydroxyindole;
(a): para-phenylenediamine,
(b): 4-hydroxy-2-methylindole,
(c): 6-hydroxyindole;
(a): para-aminophenol,
(b): 4-hydroxy-1-N-methylindole,
(c): 6-hydroxyindole;
(a): para-aminophenol,
(b): 4-hydroxy-2-methylindole,
(c): 6-hydroxyindole;
(a): 4-amino-3-methylphenol,
(b): 4-hydroxy-1-N-methylindole,
(c): 6-hydroxyindole;
(a): 4-amino-3-methylphenol,
(b): 4-hydroxy-2-methylindole,
(c): 6-hydroxyindole;
(a): para-toluylenediamine,
(b): 4-hydroxyindole,
(c): 6-hydroxyindole;
(a): para-toluylenediamine,
(b): 4-hydroxyindole,
(c): 4-hydroxybenzimidazole;
(a): para-toluylenediamine,
(b): 4-hydroxyindole,
(c): 6-hydroxybenzomorpholine;
(a): 4-amino-3-methylphenol,
(b): 4-hydroxyindole, (c): 6-hydroxybenzomorpholine;
(a): 2,6-dimethyl-para-phenylenediamine,
(b): 4-hydroxy-1-methylindole,
(c): 1-amino-6-methoxy-3,4-methylenedioxybenzene;
(a): 3,4-diaminopyrazole,
(b): 4-hydroxyindole,
(c): 2,6-diaminopyridine.

The oxidation bases in accordance with the invention together preferably represent approximately from 0.0005 to 12% by weight relative to the total weight of the dye composition, and even more preferably approximately from 0.005 to 6% by weight relative to this weight.

The indole coupler or couplers of formula (I) in accordance with the invention preferably represent approximately from 0.0001 to 5% by weight relative to the total weight of the dye composition and even more preferably approximately from 0.005 to 3% by weight relative to this weight.

The additional heterocyclic coupler or couplers in accordance with the invention preferably represent approximately from 0.0001 to 10% by weight relative to the total weight of the dye composition, and even more preferably approximately from 0.005 to 5% by weight relative to this weight.

The medium which is suitable for dyeing (or the support) generally comprises: water or of a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monomethyl ether and monoethyl ether, as well as aromatic alcohols such as benzyl alcohol or phenoxy-ethanol, similar products and mixtures thereof.

The solvents may be present in proportions preferably of approximately from 1 to 40% by weight relative to the total weight of the dye composition, and even more preferably of approximately from 5 to 30% by weight.

The pH of the dye composition in accordance with the invention is generally approximately from 3 to 12 and even more preferably approximately from 5 to 11. It may be adjusted to the desired value using acidifying or basifying agents usually used in the dyeing of keratin fibers.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkaline carbonates, alkanolamines such as mono-, di- and triethanolamines and derivatives thereof, sodium hydroxide, potassium hydroxide and the compounds of following formula (XI):

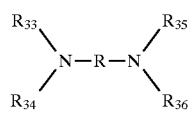

in which
R is a propylene residue optionally substituted with a hydroxyl group or a $C_1$–$C_4$ alkyl radical; $R_{33}$, $R_{34}$, $R_{35}$ and $R_{36}$, which may be identical or different, represent a hydrogen atom or a $C_1$–$C_4$ alkyl or $C_1$–$C_4$ hydroxyalkyl radical.

In addition to the dyes defined above, the dye composition in accordance with the invention may also contain other oxidation bases and/or other couplers and/or direct dyes, in particular in order to modify the shades or to enrich them with glints.

The dye composition according to the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Of course, a person skilled in the art will take care to choose this or these optional complementary compound(s) such that the advantageous properties intrinsically associated with the ternary combination in accordance with the invention are not, or are substantially not, adversely affected by the addition or additions envisaged.

The dye composition according to the invention may be in various forms, such as in the form of liquids, creams, gels or any other form which is suitable for dyeing keratin fibers, and in particular human hair.

The subject of the invention is also a process for dyeing keratin fibers, and in particular human keratin fibers such as the hair, using the dye composition as defined above. According to this process, the dye composition as defined above is applied to the fibers, the color being developed at acidic, neutral or alkaline pH using an oxidizing agent which is added only at the time of use to the dye composition or which is present in an oxidizing composition that is applied simultaneously or sequentially in a separate manner, i.e., the oxidizing composition is applied from a separate dispenser than the dye composition, either at the same time (simultaneously) as the dye composition or sequentially with it.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibers and is left in place for 3 to 50 minutes approximately, preferably 5 to 30 minutes approximately, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibers preferably varies approximately from 3 to 12 and even more preferably from 5 to 11. It is adjusted to the desired value using acidifying or basifying agents usually used in the dyeing of keratin fibers and as defined above.

The oxidizing composition as defined above may also include various adjuvants conventionally used in compositions for dyeing the hair and as defined above.

The composition which is finally applied to the keratin fibers may be in various forms, such as in the form of liquids, creams, gels or any other form which is suitable for dyeing keratin fibers, and in particular human hair.

Another subject of the invention is a multi-compartment device or dyeing kit or any other multi-compartment packaging system, a first compartment of which contains the dye composition as defined above and a second compartment of which contains the oxidizing composition as defined above. These devices may be equipped with a means which makes it possible to deliver the desired mixture onto the hair, such as the devices described in patent FR-2,586,913 assigned to the present assignee.

The examples which follow are intended to illustrate the invention without, however, limiting the scope thereof.

EXAMPLES

Example 1 to 5 of Dyeing in an Alkaline Medium

The following dye compositions were prepared (contents in grams):

| EXAMPLE | 1 | 2 | 3 | 4 | 4 |
|---|---|---|---|---|---|
| Para-aminophenol | 0.2 | | | | |
| 2-(β-Hydroxyethyl)-para-phenylenediamine dihydrochloride | | 0.3 | | | |
| 4-Amino-3-methylphenol | | | 0.3 | | |
| 2,6-Dimethyl-para-phenylenediamine dihydrochloride | | | | 1.0 | |
| 3,4-Diaminopyrazole dihydrochloride | | | | | 0.3 |
| 4-Hydroxyindole | 0.1 | 0.2 | 0.25 | | 0.05 |
| 4-Hydroxy-1-methylindole | | | | 0.5 | |
| 6-Hydroxyindole | 0.1 | | | | |
| 4-Hydroxybenzimidazole hydrobromide | | 0.1 | | | |
| 6-Hydroxybenzomorpholine | | 0.05 | | | |
| 1-Amino-6-methoxy-3,4-methylenedioxybenzene hydrochloride | | | | 0.5 | |
| 2,6-Diaminopyridine | | | | | 0.25 |
| Common dye support | (*) | (*) | (*) | (*) | (*) |
| Demineralized water qs. | 100 g | 100 g | 100 g | 100 g | 100 g |

| (*): Common dye support: | |
|---|---|
| Oleyl alcohol polyglycerolated with 2 mol of glycerol | 4.0 g |
| Oleyl alcohol polyglycerolated with 4 mol of glycerol, containing 78% of active material (AM) | 5.69 g AM |
| Oleic acid | 3.0 g |
| Oleylamine containing 2 mol of ethylene oxide, sold under the trade name Ethomeen O12 by the company AKZO | 7.0 g |
| Diethylaminopropyl laurylaminosuccinamate, sodium salt, containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution, containing 35% of AM | 0.455 g AM |
| Ammonium acetate | 0.8 g |
| Antioxidant, sequestering agent | qs |
| Fragrance, preserving agent | qs |
| Aqueous ammonia containing 20% of $NH_3$ | 10.0 g |

Each dye composition was mixed, at the time of use, with an equal weight amount of 20-volumes aqueous hydrogen peroxide solution (6% by weight).

Each resulting composition had a pH of approximately 10.2, and was applied for 30 minutes to locks of natural or permanent-waved grey hair containing 90% white hairs. The locks of hair were then rinsed, washed with a standard shampoo and then dried.

The locks of hair were dyed in the shades featured in the table below:

| EXAMPLE | SHADE ON NATURAL HAIR | SHADE ON PERMANENT-WAVED HAIR |
|---|---|---|
| 1 | Slightly iridescent coppery beige | Coppery slightly iridescent |
| 2 | Slightly bluish ash | Strong bluish ash |
| 3 | Slightly iridescent | Iridescent |
| 4 | Matt ashen dark blonde | Matt natural brown |
| 5 | Strong fuchsia pink | Very strong fuchsia pink |

Example 6 of Dyeing in an Acidic Medium

The following dye composition was prepared (contents in grams):

| EXAMPLE | 6 |
|---|---|
| 2,6-Dimethyl-para-phenylenediamine dihydrochloride | 0.5 |
| 4-Hydroxyindole | 0.3 |
| 6-Hydroxyindole | 0.2 |
| Dye support | (**) |
| Demineralized water qs | 100 g |

| (**): Dye support: | |
|---|---|
| Oleyl alcohol polyglycerolated with 2 mol of glycerol | 4.0 g |
| Oleyl alcohol polyglycerolated with 4 mol of glycerol, containing 78% of active material (AM) | 5.69 g AM |
| Oleic acid | 3.0 g |
| Oleylamine containing 2 mol of ethylene oxide, sold under the trade name Ethomeen O12 by the company AKZO | 7.0 g |
| Diethylaminopropyl laurylaminosuccinamate, sodium salt, containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution, containing 35% of AM | 0.455 g AM |
| Ammonium acetate | 0.8 g |
| Antioxidant, sequestering agent | qs |
| Fragrance, preserving agent | qs |
| Monoethanolamine qs | pH 9.8 |

The dye composition was mixed, at the time of use, with an equal weight amount of 20-volumes aqueous hydrogen peroxide solution (6% by weight), the pH of which had been adjusted to between 1 and 1.5 with 2.5 g of orthophosphoric acid per 100 g of aqueous hydrogen peroxide solution.

The resulting composition had a pH of 6.6, and was applied for 30 minutes to locks of natural or permanent-waved grey hair containing 90% white hairs. The locks of hair were then rinsed, washed with a standard shampoo and then dried.

The locks of hair were dyed in the shades featured in the table below:

| EXAMPLE | SHADE ON NATURAL HAIR | SHADE ON PERMANENT-WAVED HAIR |
|---|---|---|
| 6 | Iridescent ashen dark blonde | Purplish-ashen light brown |

What is claimed is:

1. A composition for the oxidation dyeing of keratin fibers, said composition comprising, in a medium which is suitable for dyeing:

(a) at least one oxidation base,
(b) at least one coupler selected from indole couplers of the following formula (I) and acid addition salts thereof:

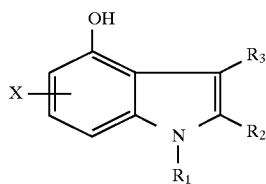

in which:
R$_1$ represents a hydrogen atom or a C$_1$–C$_4$ alkyl radical,
R$_2$ and R$_3$, which may be identical or different, represent a hydrogen atom or a C$_1$–C$_4$ alkyl, carboxyl or (C$_1$–C$_4$) alkoxycarbonyl radical,
X represents a hydrogen or halogen atom or a C$_1$–C$_4$ alkyl, C$_1$–C$_{18}$ alkoxy or acetylamino radical; and
(c) at least one additional heterocyclic coupler selected from:
    (i) the indole derivatives of the formula (II), and the acid-addition salts thereof:

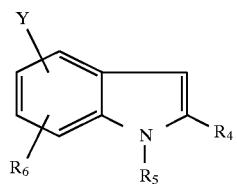

in which:
R$_4$ and R$_5$, which may be identical or different, represent a hydrogen atom or a C$_1$–C$_4$ alkyl radical;
R$_6$ represents a hydrogen atom or a C$_1$–C$_4$ alkyl or hydroxyl radical;
Y represents a hydroxyl radical or a radical NHR$_7$ in which R$_7$ represents a hydrogen atom or a C$_1$–C$_4$ alkyl or C$_1$–C$_4$ hydroxyalkyl radical; with the proviso that:
    when R$_6$ denotes hydroxyl, it then occupies the 6-position, Y denotes hydroxyl and occupies the 5-position and R$_4$ and R$_5$ represent a hydrogen atom,
    when Y denotes hydroxyl, it then occupies the 6- or 7-position, and R$_6$ is other than hydroxyl,
    when Y denotes amino, it then occupies the 4-, 6- or 7-position;
    (ii) the benzimidazole derivatives of the formula (III), and the acid-addition salts thereof:

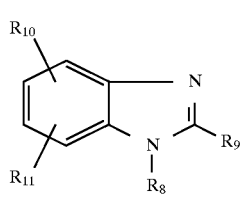

in which:
R$_8$ represents a hydrogen atom or a C$_1$–C$_4$ alkyl radical,
R$_9$ represents a hydrogen atom or a C$_1$–C$_4$ alkyl or phenyl radical,
R$_{10}$ represents a hydroxyl, amino or methoxy radical,
R$_{11}$ represents a hydrogen atom or a hydroxyl, methoxy or C$_1$–C$_4$ alkyl radical;
with the proviso that:
    when R$_{10}$ denotes an amino radical, it then occupies the 4-position,
    when R$_{10}$ occupies the 4-position, R$_{11}$ then occupies the 7-position,
    when R$_{10}$ occupies the 5-position, R$_{11}$ then occupies the 6-position;
    (iii) the benzomorpholine derivatives of the formula (IV), and the acid-addition salts thereof:

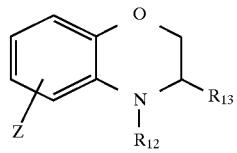

in which:
R$_{12}$ and R$_{13}$, which may be identical or different, represent a hydrogen atom or a C$_1$–C$_4$ alkyl radical,
Z represents a hydroxyl or amino radical;
    (iv) the pyridine derivatives of the formula (V), and the acid-addition salts thereof:

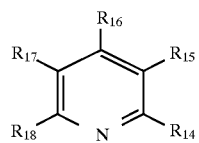

in which:
R$_{14}$ represent is a hydrogen atom, a hydroxyl, C$_1$–C$_4$ alkoxy, C$_1$–C$_4$ monohydroxyalkoxy, C$_2$–C$_4$ polyhydroxyalkoxy or amino radical or the —OCH$_2$CH$_2$COCH$_2$CH$_2$OH) group,
R$_{15}$ and R$_{17}$, which may be identical or different, represent a hydrogen atom or a hydroxyl, amino or C$_1$–C$_4$ alkyl radical,
R$_{16}$ represents a hydrogen atom or a C$_1$–C$_4$ alkyl radical,
R$_{18}$ represents a hydrogen atom or a hydroxyl, C$_1$–C$_4$ alkoxy, C$_1$–C$_4$ monohydroxyalkoxy, C$_2$–C$_4$ polyhydroxyalkoxy or amino radical,
with the proviso that when R$_{14}$ represents a polyhydroxyalkoxy radical or the —OCH$_2$CH$_2$COCH$_2$CH$_2$OH group, R$_{15}$ and R$_{17}$ then represent an amino radical;
and wherein the compounds of formula (V) contain not more than two substituted or unsubstituted amino groups or not more than two hydroxyl groups or not more than one amino group and one hydroxyl group per molecule; said amino, hydroxyl, or amino and hydroxyl groups necessarily being in a meta position relative to each other;
    (v) the indoline derivatives chosen from 6-hydroxyindoline, 6-aminoindoline and 5,6-dihydroxyindoline, and the acid-addition salts thereof;
    (vi) the quinoline derivatives of the formula (VI), and the acid-addition salts thereof:

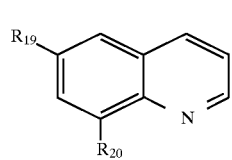

in which:
R$_{19}$ denotes a hydroxyl or C$_1$–C$_4$ alkoxy radical,
R$_{20}$ denotes a hydrogen atom or amino radical; and
    (vii) the sesamol derivatives of the formula (VII), and the acid-addition salts thereof:

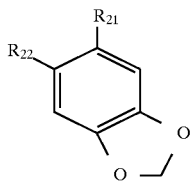

(VII)

in which:

$R_{21}$ denotes a hydroxyl or amino radical, and $R_{22}$ denotes a halogen atom or a $C_1$–$C_4$ alkoxy radical, wherein said at least one oxidation base, said at least one coupler, and said at least one additional heterocyclic coupler are present in an amount effective to dye said keratin fibers.

2. A composition according to claim 1, wherein said keratin fibers are human keratin fibers.

3. A composition according to claim 2, wherein said human keratin fibers are hair.

4. A composition according to claim 1, wherein said at least one oxidation base is selected from para-phenylenediamines, bis(phenyl)alkylenediamines, para-aminophenols, ortho-aminophenols, heterocyclic bases, and the acid-addition salts thereof.

5. A composition according to claim 4, wherein said para-phenylenediamines are selected from the compounds corresponding to the formula (VII), and the acid-addition salts thereof:

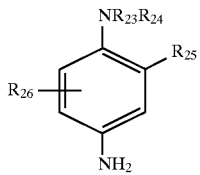

(VIII)

in which:

$R_{23}$ represents a hydrogen atom or a $C_1$–$C_4$ alkyl, $C_1$–$C_4$ monohydroxyalkyl, $C_2$–$C_4$ polyhydroxyalkyl or $(C_1$–$C_4)$alkoxy$(C_1$–$C_4)$alkyl radical, $R_{24}$ represents a hydrogen atom or a $C_1$–$C_4$ alkyl, $C_1$–$C_4$ monohydroxyalkyl or $C_2$–$C_4$ polyhydroxyalkyl radical, $R_{25}$ represents a hydrogen atom, a halogen atom, or a $C_1$–$C_4$ alkyl, sulpho, carboxyl, $C_1$–$C_4$ monohydroxyalkyl or $C_1$–$C_4$ hydroxyalkoxy radical, $R_{26}$ represents a hydrogen atom or a $C_1$–$C_4$ alkyl radical.

6. A composition according to claim 5, wherein said para-phenylenediamines of formula (VII) are selected from para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-(β-methoxyethyl)aminobenzene, N,N'-bis(β-hydroxyethyl)-N,N'-bis(4'-aminophenyl)-1,3-diamino-2-propanol, 2-chloro-para-phenylenediamine, and the acid-addition salts thereof.

7. A composition according to claim 4, wherein said bis(phenyl)alkylenediamines are selected from the compounds corresponding to the formula (IX), and the acid-addition salts thereof:

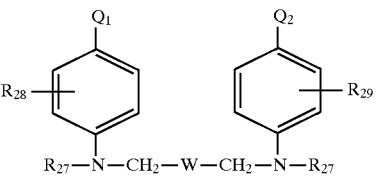

(IX)

in which:

$Q_1$ and $Q_2$, which may be identical or different, represent a hydroxyl radical or a radical $NHR_{30}$ in which $R_{30}$ represents a hydrogen atom or a $C_1$–$C_4$ alkyl radical, $R_{27}$ independently represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue may be substituted, $R_{28}$ and $R_{29}$, which may be identical or different, represent a hydrogen or halogen atom or a $C_1$–$C_4$ alkyl radical, W represents a radical, said radical being —$(CH_2)_n$—; —$(CH_2)_m$—O—$(CH_2)_m$—; —$(CH_2)_m$—CHOH—$(CH_2)_m$— or

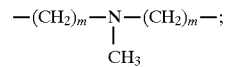

in which n is an integer from 0 to 8 and m is independently an integer from 0 to 4.

8. A composition according to claim 7, wherein said bis(phenyl)alkylenediamines of formula (IX) are selected from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methyl-aminophenyl)tetramethylenediamine, N,N'-bis(ethyl)-N,N'-bis(4'-amino-3'-methylphenyl)ethylenediamine, and the acid-addition salts thereof.

9. A composition according to claim 4, wherein said para-aminophenols are selected from the compounds corresponding to the following formula (X), and the acid-addition salts thereof:

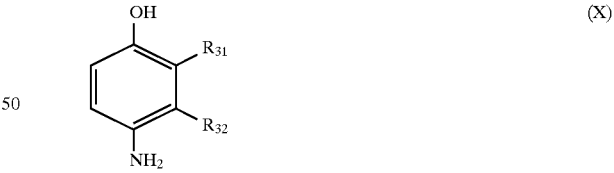

(X)

in which:

$R_{31}$ represents a hydrogen atom or a $C_1$–$C_4$ alkyl, $C_1$–$C_4$ monohydroxyalkyl, $(C_1$–$C_4)$alkoxy$(C_1$–$C_4)$alkyl or $C_1$–$C4$ aminoalkyl radical, $R_{32}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $(C_1$–$C_4)$alkoxy$(C_1$–$C_4)$alkyl radical, wherein at least one of the radicals $R_{31}$ or $R_{32}$ represents a hydrogen atom.

10. A composition according to claim 9, wherein the para-aminophenols of formula (X) are selected from para-aminophenol, 4-amino-3-methylphenol, 4-amino-3-fluorophenol, 4-amino-3-hydroxymethylphenol, 4-amino-2- methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, and the acid-addition salts thereof.

11. A composition according to claim 4, wherein said ortho-aminophenols are selected from 2-aminophenol, 2-amino-1-hydroxy-5-methylbenzene, 2-amino-1-hydroxy-6-methylbenzene, 5-acetamido-2-aminophenol, and the acid-addition salts thereof.

12. A composition according to claim 4, wherein said heterocyclic bases are selected from pyridine derivatives, pyrimidine derivatives and pyrazole derivatives, and the acid-addition salts thereof.

13. A composition according to claim 12, wherein the heterocyclic oxidation bases are selected from 2,5-diaminopyridine, 2,4,5,6-tetraaminopyrimidine, 4-hydroxy-2,5,6-triamino-pyrimidine, 4,5-diamino-1-methylpyrazole and 3,4-diaminopyrazole, and the acid-addition salts thereof.

14. A composition according to claim 1, wherein said indole couplers of formula (I) are selected from 4-hydroxyindole, 4-hydroxy-5-ethoxyindole, 4-hydroxy-5-methoxyindole, 4-hydroxy-1-methyl-5-ethoxyindole, 4-hydroxy-2-ethoxycarbonyl-5-ethoxyindole, 4-hydroxy-2-methyl-5-ethoxyindole, 4-hydroxy-5-methylindole, 4-hydroxy-2-methylindole, and 4-hydroxy-1-methylindole.

15. A composition according to claim 1, wherein said indole derivatives of formula (II) are selected from 6-hydroxyindole, 7-aminoindole, 6-aminoindole, 7-hydroxyindole, 7-ethyl-6-(β-hydroxyethyl)aminoindole, 4-aminoindole, 6-hydroxy-1-methylindole and 5,6-dihydroxyindole.

16. A composition according to claim 1, wherein the benzimidazole derivatives of formula (III) are selected from 4-hydroxy-benzimidazole, 4-aminobenzimidazole, 4-hydroxy-7-methylbenzimidazole, 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxybenzimidazole, 4,7-dihydroxy-benzimidazole, 4,7-dihydroxy-1-methylbenzimidazole, 4,7-dimethoxybenzimidazole, 5,6-dihydroxy-1-methyl-benzimidazole, 5,6-dihydroxy-2-methylbenzimidazole and 5,6-dimethoxybenzimidazole.

17. A composition according to claim 1, wherein the benzomorpholine derivatives of formula (IV) are selected from 6-hydroxybenzomorpholine, N-methyl-6-hydroxybenzo-morpholine and 6-aminobenzomorpholine.

18. A composition according to claim 1, wherein the pyridine derivatives of formula (V) are selected from 2,6-dihydroxy-4-methylpyridine, 2,6-dihydroxy-3,4-dimethylpyridine, 3,5-diamino-2,6-dimethoxypyridine, 2,6-bis(β-hydroxyethyl)oxy-3,5-diaminopyridine, 3-amino-2,6-dimethoxy-5-hydroxypyridine, 2,6-diaminopyridine, 3-oxo-5-(3',5'-diamino-2'-pyridyloxy)pentanol and 3-(3',5'-diamino-2'-pyridyloxy)-2-hydroxypropanol.

19. A composition according to claim 1, wherein the quinoline derivatives of formula (VI) are selected from 6-hydroxy-quinoline and 8-amino-6-methoxyquinoline.

20. A composition according to claim 1, wherein the sesamol derivatives of formula (VII) are selected from 2-bromo-4,5-methylenedioxyphenol and 1-amino-6-methoxy-3,4-methylenedioxybenzene.

21. A composition according to claim 1, wherein the acid-addition salts are selected from the hydrochlorides, hydrobromides, sulphates and tartrates.

22. A composition according to claim 1, wherein said composition includes at least one of the following ternary combinations:

(a): para-phenylenediamine,
(b): 4-hydroxyindole,
(c): 6-hydroxyindole;
(a): para-phenylenediamine,
(b): 4-hydroxyindole,
(c): 4-hydroxybenzimidazole;
(a): para-phenylenediamine,
(b): 4-hydroxyindole,
(c): 6-hydroxybenzomorpholine;
(a): para-aminophenol,
(b): 4-hydroxyindole,
(c): 6-hydroxyindole;
(a): 4-amino-3-methylphenol,
(b): 4-hydroxyindole,
(c): 6-hydroxyindole;
(a): 2-aminophenol,
(b): 4-hydroxyindole,
(c): 6-hydroxyindole;
(a): 4,5-diamino-1-methylpyrazole,
(b): 4-hydroxyindole,
(c): 6-hydroxyindole;
(a): 4,5-diamino-1-methylpyrazole,
(b): 4-hydroxyindole,
(c): 4-hydroxybenzimidazole;
(a): 4,5-diamino-1-methylpyrazole,
(b): 4-hydroxyindole,
(c): 6-hydroxybenzomorpholine;
(a): 2,6-dimethyl-para-phenylenediamine,
(b): 4-hydroxyindole,
(c): 6-hydroxyindole;
(a): 2,6-dimethyl-para-phenylenediamine,
(b): 4-hydroxyindole,
(c): 4-hydroxybenzimidazole;
(a): 2,6-dimethyl-para-phenylenediamine,
(b): 4-hydroxyindole,
(c): 6-hydroxybenzomorpholine,
(a): 2-β-hydroxyethyl-para-phenylenediamine,
(b): 4-hydroxyindole,
(c): 6-hydroxyindole;
(a): 2-β-hydroxyethyl-para-phenylenediamine,
(b): 4-hydroxyindole,
(c): 4-hydroxybenzimidazole;
(a): para-phenylenediamine,
(b): 4-hydroxy-1-N-methylindole,
(c): 6-hydroxyindole;
(a): para-phenylenediamine,
(b): 4-hydroxy-2-methylindole,
(c): 6-hydroxyindole;
(a): para-aminophenol,
(b): 4-hydroxy-1-N-methylindole,
(c): 6-hydroxyindole;
(a): para-aminophenol,
(b): 4-hydroxy-2-methylindole,
(c): 6-hydroxyindole;
(a): 4-amino-3-methylphenol,
(b): 4-hydroxy-1-N-methylindole,
(c): 6-hydroxyindole;
(a): 4-amino-3-methylphenol,
(b): 4-hydroxy-2-methylindole,
(c): 6-hydroxyindole;
(a): para-toluylenediamine,
(b): 4-hydroxyindole,
(c): 6-hydroxyindole;
(a): para-toluylenediamine,
(b): 4-hydroxyindole,
(c): 4-hydroxybenzimidazole;

(a): para-toluylenediamine,
(b): 4-hydroxyindole,
(c): 6-hydroxybenzomorpholine;
(a): 4-amino-3-methylphenol,
(b): 4-hydroxyindole,
(c): 6-hydroxybenzomorpholine;
(a): 2,6-dimethyl-para-phenylenediamine,
(b): 4-hydroxy-1-methylindole,
(c): 1-amino-6-methoxy-3,4-methylenedioxybenzene;
(a): 3,4-diaminopyrazole,
(b): 4-hydroxyindole,
(c): 2,6-diaminopyridine.

23. A composition according to claim 1, wherein said at least one oxidation base represents from 0.0005 to 12% by weight relative to the total weight of the dye composition.

24. A composition according to claim 23, wherein said at least one oxidation base represents from 0.005 to 6% by weight relative to the total weight of the dye composition.

25. A composition according to claim 1, wherein said at least one coupler represents from 0.0001 to 5% by weight relative to the total weight of the dye composition.

26. A composition according to claim 25, wherein said at least one coupler represents from 0.005 to 3% by weight relative to the total weight of the dye composition.

27. A composition according to claim 1, wherein said at least one additional heterocyclic coupler represents from 0.0001 to 10% by weight relative to the total weight of the dye composition.

28. A composition according to claim 27, wherein said at least one additional heterocyclic coupler represents from 0.005 to 5% by weight relative to the total weight of the dye composition.

29. A composition according to claim 1, wherein the medium which is suitable for dyeing comprises water or a mixture of water and at least one organic solvent selected from $C_1$–$C_4$ lower alkanols, glycerol, glycols and glycol ethers, aromatic alcohols, and mixtures thereof.

30. A composition according to claim 1, wherein said composition has a pH from 3 to 12.

31. A process for dyeing keratin fibers, said process comprising the steps of:
    applying to said fibers an amount effective for developing color of a dye composition as defined in claim 1;
    developing color at acidic, neutral or alkaline pH using an effective amount of an oxidizing agent which is added to the dye composition only at the time of use or which is present in an oxidizing composition that is applied:
    (i) separately from the dye composition at the same time that said dyeing composition is applied to said fibers or
    (ii) sequentially with the dye composition.

32. A process according to claim 31, wherein said keratin fibers are human keratin fibers.

33. A process according to claim 32, wherein said human keratin fibers are hair.

34. A process according to claim 31, wherein said oxidizing agent is selected from hydrogen peroxide, urea peroxide, alkali metal bromates and persalts.

35. A process according to claim 34, wherein said persalts are perborates or persulphates.

36. A multi-compartment device, or multi-compartment dyeing kit, comprising a first compartment containing a dye composition as defined in claim 1 and a second compartment containing an oxidizing composition.

* * * * *

UNITED STATES PATENT AND TRADEMARK OFFICE
CERTIFICATE OF CORRECTION

PATENT NO. : 5,769,903
DATED : June 23, 1998
INVENTOR(S) : Audousset et al.

It is certified that error appears in the above-identified patent and that said Letters Patent is hereby corrected as shown below:

Claim 1, column 14, line 32, after "OH", delete ")".

Claim 5, column 15, line 29, "(VII)" should read --(VIII)--.

Claim 6, column 15, line 52, "(VII)" should read --(VIII)--.

Claim 9, column 16, line 57, "$C_1$-C4" should read --$C_1$-$C_4$--.

Signed and Sealed this

Twenty-fifth Day of August, 1998

Attest:

BRUCE LEHMAN

*Attesting Officer*   *Commissioner of Patents and Trademarks*